United States Patent
Zeng et al.

(10) Patent No.: US 9,278,055 B2
(45) Date of Patent: Mar. 8, 2016

(54) ENCAPSULATION OF PERSONAL CARE ACTIVES

(71) Applicants: DOW GLOBAL TECHNOLOGIES LLC, Midland, MI (US); ROHM AND HAAS COMPANY, Philadelphia, PA (US)

(72) Inventors: Fanwen Zeng, Belle Mead, NJ (US); Charles Jones, Yardley, PA (US); Diane Routzahn, Levittown, PA (US); Stephen L. Wilson, Zionsville, IN (US)

(73) Assignees: Dow Global Technologies LLC, Midland, MI (US); Rohm and Haas Chemicals LLC, Philadelphia, PA (US)

( * ) Notice: Subject to any disclaimer, the term of this patent is extended or adjusted under 35 U.S.C. 154(b) by 0 days.

(21) Appl. No.: 14/352,108

(22) PCT Filed: Oct. 16, 2012

(86) PCT No.: PCT/US2012/060376
§ 371 (c)(1),
(2) Date: Apr. 16, 2014

(87) PCT Pub. No.: WO2013/059167
PCT Pub. Date: Apr. 25, 2013

(65) Prior Publication Data
US 2014/0271752 A1    Sep. 18, 2014

Related U.S. Application Data

(60) Provisional application No. 61/548,907, filed on Oct. 19, 2011.

(51) Int. Cl.
| | |
|---|---|
| *A61K 8/02* | (2006.01) |
| *A61Q 17/04* | (2006.01) |
| *A61K 8/84* | (2006.01) |
| *A61K 8/86* | (2006.01) |
| *A61K 8/11* | (2006.01) |
| *B01J 13/14* | (2006.01) |
| *B01J 13/16* | (2006.01) |
| *A61K 8/35* | (2006.01) |

(52) U.S. Cl.
CPC ............. *A61K 8/0241* (2013.01); *A61K 8/11* (2013.01); *A61K 8/35* (2013.01); *A61K 8/84* (2013.01); *A61K 8/86* (2013.01); *A61Q 17/04* (2013.01); *B01J 13/14* (2013.01); *B01J 13/16* (2013.01); *A61K 2800/412* (2013.01); *A61K 2800/56* (2013.01)

(58) Field of Classification Search
None
See application file for complete search history.

(56) References Cited

U.S. PATENT DOCUMENTS

| | | | |
|---|---|---|---|
| 5,925,464 | A | 7/1999 | Mulqueen et al. |
| 2007/0220686 | A1 | 9/2007 | Jeanne-Rose et al. |
| 2009/0203528 | A1 | 8/2009 | Xu et al. |
| 2009/0247409 | A1 | 10/2009 | Xu et al. |
| 2009/0311336 | A1 | 12/2009 | Jones et al. |
| 2013/0337023 | A1* | 12/2013 | Lei et al. ................. 424/401 |

FOREIGN PATENT DOCUMENTS

| | | |
|---|---|---|
| EP | 0392876 A1 | 10/1990 |
| WO | 9803065 A1 | 1/1998 |
| WO | 03101606 A1 | 12/2003 |
| WO | 2009007264 A2 | 1/2009 |
| WO | 2009091726 A1 | 7/2009 |

OTHER PUBLICATIONS

Hashemi et al. Encapsulation Processin Synthesizing Polyurea Microcapsules Containing Pesticide, Iranian Polymer Journal, vol. 10 No. 4, 2001.*
Alexandridou, S., et al., "Production of Oil-Containing Polyterephthalamide Microcapsules by Interfacial Polymerization. An Experimental Investigation of the Effectof Process Variables on the Microcapsule Size Distribution", J. Microencapsulation, 1994, vol. 11, pp. 603-614.

* cited by examiner

*Primary Examiner* — Robert A Wax
*Assistant Examiner* — Melissa Mercier
(74) *Attorney, Agent, or Firm* — Edward L. Brant

(57) ABSTRACT

Described are methods for encapsulating a personal care active, comprising preparing an aqueous phase, comprising partially hydrolyzed polyvinyl alcohol and a cosmetically acceptable non-ionic surfactant, preparing an oil phase, comprising the personal care active and isocyanate or polyisocyanate, homogenizing the aqueous phase and oil phase to form an emulsion with particles less than one micron, and forming a dispersion of polyurea core-shell particles containing the personal care active by contacting the emulsion with an aqueous amine solution.

10 Claims, No Drawings

ENCAPSULATION OF PERSONAL CARE ACTIVES

CROSS-REFERENCE TO RELATED APPLICATIONS

This application claims priority to and is a 371 U.S.C. §371 national phase application of International Application No. PCT/US/2012/060376, filed on Oct. 16, 2012, which claims the priority benefit of U.S. Provisional Application No. 61/548,907, filed on Oct. 19, 2011, each of which is incorporated herein by reference.

FIELD

The present invention relates to personal care compositions with encapsulated actives, and in particular, sun care actives.

BACKGROUND

The effectiveness of certain sun care actives, for example, sunscreens, is well understood, however, many are also associated with certain drawbacks, such as skin sensitization, or incompatibility with other components typically found in personal care compositions. One solution to avoid such drawbacks is to encapsulate the sun care actives, however, processing conditions can be a challenge, and resulting particle size is either marred by a large particle size distribution or particles that are too large.

Therefore, what is needed are new or improved methods for encapsulating personal care actives.

DETAILED DESCRIPTION

In one embodiment, the present invention provides methods for encapsulating a personal care active, comprising preparing an aqueous phase, comprising partially hydrolyzed polyvinyl alcohol and a cosmetically acceptable non-ionic surfactant, preparing an oil phase, comprising the personal care active and isocyanate or polyisocyanate, homogenizing the aqueous phase and oil phase to form an emulsion with particles less than one micron, and forming a dispersion of polyurea core-shell particles containing the personal care active by contacting the emulsion with an aqueous amine solution.

In one embodiment, emulsifying the oil phase in the aqueous phase does not require high pressure homogenization.

Non-limiting examples of non-ionic surfactants include ethylene oxide, propylene oxide, butylene oxide, fatty alcohol ethoxylates (alkoxylates), fatty acid esters (and alkoxylates of fatty acid esters), unsaturated polyalkoxyalkyl ethers, alkoxylated amines, ethylene oxide propylene oxide copolymers, fatty acid alkoxylates (PAG esters, specifically PEG esters), tall oil and rosin ester alkoxylates, alkyl phenol alkoxylates, and substituted phenol alkoxylates. In one embodiment, the non-ionic surfactant is a polyoxyethylene alkyl ether under the trade name of ALTOX 4991™ from Croda. In another embodiment, the non-ionic surfactant is a secondary alcohol ethoxylate such as TERGITOL™ 15-S-40 from The Dow Chemical Company. In one embodiment, the surfactant is present in an amount of from about 1 to about 7.5 weight percent, preferably from about 2.5 to 5 weight percent based on the total weight of the aqueous phase.

In one embodiment, the partially hydrolyzed polyvinyl alcohol is present in an amount of from 1 to 15 weight percent, preferably from 2.5 to 12.5 weight percent, and more preferably from 5 to 10 weight percent, based on the total weight percent of the aqueous phase. In addition to partially hydrolyzed polyvinyl alcohol (PVA), the aqueous phase may optionally further comprise polyvinyl pyrrolidone, copolymers of vinyl pyrrolidone and acetate, copolymers of vinyl pyrrolidone, vinyl acetate and vinyl alcohol, copolymers of acrylic acid and polyethyleneoxide), copolymers of alkyl(meth)acrylate), lignosulphonate, copolymers of maleic anhydride and methyl vinyl ether, copolymers of maleic anhydride and diisobutylene, polystyrene sulphonate, polyalkyl cellulose or polycarboxyalkyl cellulose.

In one embodiment, the isocyanate or polyisocyanate undergo an interfacial polymerization reaction to form a core-shell. Exemplary isocyanates include, but are not limited to, toluene diisocyanate (TDI), diisocyanato-diphenylmethane (MDI), derivatives of MDI such as polymethylene polyphenylisocyanate that contains MDI, an example of which is PAPI 27™ polymeric MDI (The Dow Chemical Company), isophorone diisocyanate, 1,4-diisocyanatobutane, phenylene diisocyanate, hexamethylene diisocyanate, 1,3-bis(isocyanatomethyl)benzene, 1,8-disocyanatooctane, 4,4'-methylenebis(phenyl isocyanate), 4,4'-methylenebis(cyclohexyl isocyanate) and mixtures thereof. In another embodiment the isocyanate is a polyisocyanate selected from a group of 4,4'-diisocyanatodiphenylmethane, 2,4'-diisocyanatodiphenylmethane, p-phenylene diisocyanate, 2,6-toluene diisocyanate, polyphenyl polymethylene polyisocyanate, 1,3-bis(isocyanatomethyl)cyclohexane, 1,4-diisocyanatocyclohexane, hexamethylene diisocyanate, 1,5-naphthalene diisocyanate, 3,3'-dimethyl-4,4'-biphenyl diisocyanate, 4,4'-diisocyanatodicyclohexylmethane, 2,4'-diisocyanatodicyclohexylmethane, isophorone diisocyanate, or 2,4-toluene diisocyanate, or a combination thereof.

Personal care actives include emollients, moisturizers, fragrances, vitamins, anti-aging actives, and sunscreens typically used in personal care compositions in amounts of which falls within the regulatory approved limits. In a preferred embodiment, the personal care agent is a sunscreen agent. Examples of sunscreen agents include, but are not limited to, p-aminobenzoic acid as well as salts and esters thereof; o-aminobenzoic acid and o-aminobenzoates (including methyl, menthyl, phenyl, benzyl, phenylethyl, linalyl, terpinyl, and cyclohexenyl esters thereof); salicylic acid and salicylates (including octyl, amyl, phenyl, benzyl, menthyl, glyceryl, and dipropyleneglycol esters thereof); cinnamic acid and derivatives thereof (including methyl and benzyl esters, alkyl alkoxycinnamates such as octyl methoxycinnamate (also known as 2-ethylhexyl-4-methoxycinnamate), alpha-phenyl cinnamonitrile, and butyl cinnamoyl pyruvate); dihydroxycinnamic acid and its derivatives; trihydroxycinnamic acid and its derivatives; diphenylbutadiene and stilbene; dibenzalacetone and benzalacetophenone; I naphthosulfonates (such as sodium salts of 2-naphthol-3,6-disulfonic acid and 2-naphthnol 6,8-disulfonic acid); dihydroxynaphthoic acid and its salts; o- and p-hydroxydiphenyldisulfonates; coumarin and derivatives thereof (such as 7-hydroxy, 7-methyl, and 3-phenyl coumarin); diazoles; quinine salts; quinoline and derivatives thereof; hydroxy- or alkoxybenzophenones; uric and vilouric acids; tannic acid and derivatives thereof; hydroquinone; benzophenones (such as oxybenzone, sulisobenzone, dioxybenzone, benzoresorcinol,2,2',4,4'-tetrahydroxybenzophenone, 2,2'-dihydroxy-4,4' dimethoxybenzophenone, octabenzone, 4-isopropyldibenzoylmethane,-4-butylmethoxydibenzoylmethane, etocrylene, and 4-isopropyl-dibenzoylmethane), and mixtures thereof. In some embodiments, the sunscreen agents include ethylhexyl salicylate, homosalate, butyl methoxydibenzoylmethane, octocrylene, phenylbenzimidazole sulfonic acid, benzophenone-3, benzophenone-4, benzophenone-5, n-hexyl 2-(4-diethylamino-2-hydroxybenzoyl)benzoate, 4-methylbenzylidene camphor, terephthalylidene dicamphor sulfonic acid, disodium phenyl dibenzimidazole tetrasulfonate, methylene bis-benzotriazolyl tetramethylbutylphenol, bis-ethylhexyloxyphenol methoxyphenyl triazine, ethylhexyl triazone, diethylhexyl butamido triazone, 2,4,6-tris (dineopentyl 4'-aminobenzalmalonate)-s-triazine, 2,4,6-tris (diisobutyl 4'-aminobenzalmalonate)-s-triazine, 2,4-bis(n-butyl 4'-aminobenzoate)-6-(aminopropyltrisiloxane)-s-triazine, 2,4-bis(dineopentyl 4'-aminobenzalmalonate)-6-(n-butyl 4'-aminobenzoate)-s-triazine, 2,4,6-tris(biphenyl-4-yl)-1,3,5-triazine, 2,4,6-tris(terphenyl)-1,3,5-triazine, drometrizole trisiloxane, polysilicone-15,1,1-dicarboxy (2,2'-dimethylpropyl)~4,4-diphenylbutadiene, 2,4-bis [5-1-(diraethylpropyl)benzoxazol-2-yl(4-phenyl)imino]-6-(2-ethylhexyl)-imino-1,3,5-triazine, and any mixtures thereof. In one embodiment, the sunscreen agent is paraminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide and zinc oxide, diethanolamine methoxycinnamate, digalloy trioleate, ethyl dihydroxypropyl PABA, glyceryl aminobenzoate, lawsone with dihydroxy acetone, red petrolatum, and any combinations thereof. In one preferred embodiment, the sunscreen agent is octyl methoxycinnamate.

In one embodiment, the emulsification process can be carried out at ambient temperatures. In certain embodiments, the process may require heating the oil phase, or the aqueous phase or a mixture of both to a temperature of 65° C. In certain embodiments, the temperature is in a range of 30° C. to 60° C.

The emulsion comprises emulsion particles having an average particle size (volume-average diameter of the particles determined by light scattering measurements) of less than 1 micron. In one embodiment, the average particle size is in a range of about 100 nm to about 1 micron. The emulsion particles have a single modal particle size distribution.

In one embodiment, the oil in water emulsion is contacted with one or more cross-linking agents to perform an interfacial polymerization reaction. In one embodiment, the cross-linking agent includes a hydroxyl-containing or amine-containing compound. In one embodiment, the hydroxyl-containing compound comprises water. Exemplary amine-containing compound includes water-soluble diamines, ethylenediamine, water-soluble polyamines, diethylenetriamine, triethylenetetramine, tetraethylenepentamine, pentaethylenehexamine, water-soluble polyamino acids, L-lysine, arginine, histidine, serine, threonine, polymers or oligomers of the aminoacids, water-soluble diols, ethylene glycol, propylene glycol, polyethylene oxide diol, resorcinol, water soluble polyols, 2-aminoethanol, guanidine, guanidine compounds, polyamidines and derivatives and any mixtures thereof.

In one embodiment, the aqueous dispersion has a solids content, wherein the solids content is at least about 35 weight percent of the total weight of the dispersion, preferably 55 weight percent of the total weight of the dispersion.

In some embodiments of the invention, the core of the microcapsule is at least 25% by weight of the particle, alternatively at least 35%, alternatively at least 45%, alternatively at least 50%, alternatively at least 55%, alternatively at least 60%, alternatively at least 65%, alternatively at least 70%, alternatively at least 75%, alternatively at least 80%; and in some embodiments no more than 95%, alternatively no more than 90%, alternatively no more than 85%.

In some embodiments of the invention, the core of the microcapsule contains at least two actives. In one particular embodiment, the core contains more than one UV absorber, one of which absorbs most strongly in the UV-A range (290-325 nm) and one of which absorbs most strongly in the UV-B range (325-400 nm). One preferred UV-A absorber is avobenzene, and one preferred UV-B absorber is homosalate (3,3,5-trimethylcyclohexyl salicylate). When avobenzone is present in the particle, preferably octyl methoxycinnamate is not present.

EXAMPLES

Example 1

Microparticles of the present invention are listed in TABLE 1.

TABLE 1

| Sample No. | Partially hydrolyzed PVA conc. (aqueous phase) | Surfactant | Surfactant conc. (aqueous phase) | oil/aqueous phase ratio | PS $(d_{-0.5})$ (µm) |
|---|---|---|---|---|---|
| 1 | 5% | ALTOX 4991 ™ | 5% | 35/65 | 0.34 |
| 2 | 7.5% | ALTOX 4991 ™ | 5% | 35/65 | 0.33 |
| 3 | 10% | ALTOX 4991 ™ | 2.5% | 35/65 | 0.49 |
| 4 | 10% | ALTOX 4991 ™ | 3.75% | 35/65 | 0.37 |
| 5 | 10% | ALTOX 4991 ™ | 5% | 30/70 | 0.29 |
| 6 | 10% | ALTOX 4991 ™ | 5% | 40/60 | 0.34 |
| 7 | 10% | ALTOX 4991 ™ | 5% | 45/55 | 0.32 |
| 8 | 10% | ALTOX 4991 ™ | 5% | 50/50 | 0.36 |
| 9 | 10% | TERGITOL 15-S-40 | 5% | 40/60 | 0.41 |
| 10 | 10% | TERGITOL 15-S-40 | 5% | 45/55 | 0.41 |

An aqueous phase is prepared by first dissolving polyvinyl alcohol (PVA) (CELVOL 205 from Celanese) in water with heating to 90° C. to form a PVA solution. The PVA solution is cooled to 55° C., and then surfactant is added to form the aqueous phase, concentrations as indicated in TABLE 1.

An oil phase is prepared by first mixing UV absorbers, 1 part of Homosalate (3,3,5-Trimethylcyclohexyl 2-hydroxybenzoate (PARSOL®)), 1 part of octocrylene (2-ethylhexyl 2-cyano-3,3-diphenyl-2-propenoate (PARSOL® 340)) and 2 parts of Avobenzone (Butyl methoxydibenzoylmethane (PARSOL® 1789) with heating to 80° C. About 7 g of polymethylene polyphenylisocyanate (PAPI™ 27) is added to about 93 g of the mixture of UV absorbers at 55° C. with gentle mixing to form the oil phase.

Preparation of the emulsion and dispersion: The aqueous phase is transferred to the oil phase slowly while both are maintained at a temperature of 50° C., in a ratio as indicated in TABLE 1. The mixture is subjected to shear with a Silverson high shear homogenizer at a shear rate of 9000 rpm for 5 to 10 minutes. The emulsion is treated with a solution of 4.6 g of ethylenediamine in 41.8 g of water and mixed for 20 minutes at 50° C. to form a slurry.

The particle size and distribution of the particles of the samples are measured using a Malvern Mastersizer 2000 with 2000 µP Module. Particle size d(0.5) is reported in TABLE 1, defined as the sieve diameter at which 50% (mass or volume) of all dispersion particles will pass. A representative sample showed excellent particle size distribution, with substantially all particles under one micron.

Example 2 (Comparative)

Comparative particles are listed in TABLE 2.

TABLE 2

| S No. | Partially hydrolyzed PVA conc. (aqueous phase) | Surfactant | Surfactant conc. (aqueous phase) | oil/aqueous phase ratio | PS $(d_{-0.5})$ (µm) |
|---|---|---|---|---|---|
| 1 | 10% | — | 0 | 50/50 | 2.2 |
| 2 | 10% | — | 0 | 50/50 | 1.2 |

Compositions are prepared substantially as above in Example 1, except no non-ionic surfactant is used and the first comparative sample is sheared at a shear rate of 5500 rpm. This illustrates the present invention advantageously reduces the average particle size.

Example 3

Sunscreens of the present invention are listed in TABLE 3.

TABLE 3

| | Ingredient | Batch Y % by weight | Batch Z % by weight |
|---|---|---|---|
| A | Water, DI | 57.55 | 63.07 |
| | ACULYN 33 Acrylates Copolymer | 3.33 | 3.33 |
| | Glycerin | 1.00 | 1.00 |
| | Tetrasodium EDTA | 0.10 | 0.10 |
| | Example 1-6 (11.92% avo) | 25.17 | — |
| | Example 1-9 (15.27% avo) | — | 19.65 |
| B | CERAPHYL 41 C12-15 Alkyl Lactate | 2.00 | 2.00 |
| | GANEX V-220 VP/Eicosene Copolymer | 1.50 | 1.50 |
| | Dow Corning 344 Fluid Cyclopentasiloxane & Hexasiloxane | 2.00 | 2.00 |
| | FINSOLV TN C12-15 Alkyl Benzoate | 5.00 | 5.00 |
| | Stearic Acid | 1.50 | 1.50 |
| C | Triethanolamine, 99% | 0.85 | 0.85 |

The sunscreen formulations are prepared as emulsions. Mixing is accomplished with the use of an overhead motor, Caframo BDC 2002, and an disperser blade on a shaft with a propeller having 3 pitched blades (~45°), and a diameter of about 3.6 centimeters. Water is heated to 75° C. and the remaining phase A are added to the heated water while mixing.

Phase B components are added together and heated to 75° C. to form mixture B. At 75° C., mixtures A and B are mixed and phase C is added. The sunscreen formulation is cooled to room temperature with continuous stirring.

Example 4 (Comparative)

Comparative sunscreens from comparative particles are listed in TABLE 4.

TABLE 4

| | Ingredient | Comparative Batch A % by weight | Comparative Batch B % by weight |
|---|---|---|---|
| A | Water, DI | 63.19 | 63.14 |
| | ACULYN 33 Acrylates Copolymer | 3.33 | 3.33 |
| | Glycerin | 1.00 | 1.00 |
| | Tetrasodium EDTA | 0.10 | 0.10 |
| | Sample 2-1 (15.35% avo) | 19.53 | — |
| | Sample 2-2 (15.32% avo) | — | 19.58 |
| B | CERAPHYL 41 C12-15 Alkyl Lactate | 2.00 | 2.00 |
| | GANEX V-220 VP/Eicosene Copolymer | 1.50 | 1.50 |
| | Dow Corning 344 Fluid Cyclopentasiloxane & Hexasiloxane | 2.00 | 2.00 |
| | FINSOLV TN C12-15 Alkyl Benzoate | 5.00 | 5.00 |
| | Stearic Acid | 1.50 | 1.50 |
| C | Triethanolamine, 99% | 0.85 | 0.85 |

Compositions are prepared substantially as above in Example 3.

To measure absorbance, a quartz plate (3¼"×4" Kodak projector slide cover glass) is taken and samples from Example 3 and 4 are smeared thickly and evenly to form films. The films are drawn out from the plate and left to completely dry for about half an hour. Absorbance measurements are taken of these films using a UV spectrometer having the Labsphere 1000s program at wavelengths from 290 nanometer (nm) to 400 nm. Results are given in TABLE 5:

TABLE 5

| | A.U. |
|---|---|
| Batch Y | 3 |
| Batch Z | 2.5 |
| Comparative Batch A | 1.8 |
| Comparative Batch B | 1.8 |

The inventive sunscreens performed better than the comparatives.

The invention claimed is:

1. A method for encapsulating a personal care active, comprising:
   preparing an aqueous phase, comprising partially hydrolyzed polyvinyl alcohol and a cosmetically acceptable non-ionic surfactant;
   preparing an oil phase, comprising the personal care active and isocyanate or polyisocyanate;
   homogenizing the aqueous phase and oil phase to form an emulsion; and
   forming a dispersion of polyurea core-shell particles containing the personal care active by contacting the emulsion with an aqueous amine solution, wherein the polyurea core-shell particles have an average particle size in a range of from 100 nm to 0.49 micron.

2. The method of claim 1, wherein the step of homogenizing excludes high pressure homogenization.

3. The method of claim 1, wherein the emulsion particles have a single modal particle size distribution.

4. The method of claim 1, wherein the non-ionic surfactant comprises ethylene oxide, propylene oxide, butylene oxide, fatty alcohol ethoxylates, fatty acid esters, alkoxylates of fatty acid esters, unsaturated polyalkoxyalkyl ethers, alkoxylated amines, ethylene oxide propylene oxide copolymers, fatty acid alkoxylates, tall oil, rosin ester alkoxylates, alkyl phenol alkoxylates or substituted phenol alkoxylates.

5. The method of claim 1, wherein the non-ionic surfactant is polyoxyethylene alkyl ether or a secondary alcohol ethoxylate.

6. The method of claim 1, wherein the surfactant is present in an amount of from about 1 to about 7.5 weight percent of the aqueous phase.

7. The method of claim 1, wherein the partially hydrolyzed polyvinyl alcohol is present in an amount of from about 1 to about 15 weight percent of the aqueous phase.

8. The method of claim 1, wherein the aqueous phase further comprises polyvinyl pyrrolidone, copolymers of vinyl pyrrolidone and acetate, copolymers of vinyl pyrrolidone, vinyl acetate and vinyl alcohol, copolymers of acrylic acid and polyethyleneoxide, copolymers of alkyl(meth)acrylate, lignosulphonate, copolymers of maleic anhydride and methyl vinyl ether, copolymers of maleic anhydride and diisobutylene, polystyrene sulphonate, polyalkyl cellulose or polycarboxyalkyl cellulose.

9. The method of claim 1, wherein the personal care active is a sunscreen agent.

10. The method of claim 9, wherein the sunscreen agent is paraminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide and zinc oxide, diethanolamine methoxycinnamate, digalloy trioleate, ethyl dihydroxypropyl PABA, glyceryl aminobenzoate, lawsone with dihydroxy acetone, red petrolatum and any combinations thereof.

* * * * *